(12) United States Patent
Bertholon et al.

(10) Patent No.: US 9,050,246 B2
(45) Date of Patent: Jun. 9, 2015

(54) INJECTABLE COMBINATION OF ADRENERGIC RECEPTOR AGONISTS WITH FILLERS, FOR DECREASING SKIN REACTIONS DUE TO INJECTION

(75) Inventors: Isabelle Bertholon, Lyons (FR);
Florence Brunel, Pierre-Benite (FR);
Benjamin Herbage, La Mulatiere (FR);
Christophe Villard, Le Tignet (FR);
Sylviane Villard, legal representative, Le Tignet (FR)

(73) Assignee: Galderma Research & Development, Biot (FR)

( * ) Notice: Subject to any disclaimer, the term of this patent is extended or adjusted under 35 U.S.C. 154(b) by 0 days.

(21) Appl. No.: 13/322,803

(22) PCT Filed: May 28, 2010

(86) PCT No.: PCT/EP2010/057493
§ 371 (c)(1),
(2), (4) Date: Feb. 7, 2012

(87) PCT Pub. No.: WO2010/136594
PCT Pub. Date: Dec. 2, 2010

(65) Prior Publication Data
US 2012/0135937 A1    May 31, 2012

Related U.S. Application Data

(60) Provisional application No. 61/213,322, filed on May 29, 2009.

(51) Int. Cl.
*A61K 8/81* (2006.01)
*A61K 8/02* (2006.01)
*A61K 9/00* (2006.01)
*A61K 31/00* (2006.01)
*A61K 31/498* (2006.01)
*A61K 31/728* (2006.01)
*A61K 45/06* (2006.01)

(52) U.S. Cl.
CPC .............. *A61K 9/0014* (2013.01); *A61K 31/00* (2013.01); *A61K 31/498* (2013.01); *A61K 31/728* (2013.01); *A61K 45/06* (2013.01)

(58) Field of Classification Search
None
See application file for complete search history.

(56) References Cited

U.S. PATENT DOCUMENTS

| 8,114,898 B2 * | 2/2012 | Shanler et al. ................. 514/393 |
| 2008/0293728 A1 | 11/2008 | McIntire et al. |
| 2011/0165210 A1 * | 7/2011 | Boutros ........................ 424/401 |
| 2011/0224215 A1 * | 9/2011 | DeJovin ........................ 514/249 |

FOREIGN PATENT DOCUMENTS

| EP | 2036538 A1 | 3/2009 |
| WO | WO-9421299 A1 | 9/1994 |
| WO | WO-2006092619 A1 | 9/2006 |
| WO | WO-2007056233 A1 | 5/2007 |
| WO | WO-2009017705 A1 | 2/2009 |
| WO | WO-2009065116 A1 | 5/2009 |
| WO | WO-2009082452 A1 | 7/2009 |
| WO | WO-2009101210 A1 | 8/2009 |

OTHER PUBLICATIONS

Naoum, C. and Dasiou-Plakida, D. (2001), Dermal filler materials and botulin toxin. International Journal of Dermatology, 40: 609-621.*
EMLA (lidocaine and prilocaine) Cream Drug Label, AstraZeneca LP, Revised Apr. 2006.*
Naoum et al ("Dermal filler materials and botulin toxin" (2001) International Journal of Dermatology 40: 609-621).*
Weigert et al ("Effects of Topical Clonidine versus Brimonidine on Choroidal Blow Flow and Intraocular Pressure during Squatting" Invest. (Sep. 2007) Ophthalmol. Vis. Sci. 48(9): 4220-4225.*
Drug Label for EMLA cream, AstraZeneca LP (Apr. 2006).*
Naoum et al ("Dermal filler materials and botulin toxin" (2001 International Journal of Dermatology 40: 609-621).*
Pratap et al ("Co-injection of Clonidine Prolongs the Anesthetic Effect of Lidocaine Skin Infiltration by a Peripheral Action" (Apr. 2007) International Anesthesia Research Society 104 (4): 982-983).*
Weigert et al ("Effects of Topical Clonidine versus Brimonidine on Choroidal Blood Flow and Intraocular Pressure during Squatting" Invest. (Sep. 2007) Ophthalmol. Vis. Sci. 48(9): 4220-4225).*
Naoum (International Journal of Dermatology (2001) 40: 609-621).*
Pratap (International Anesthesia Research Society (Apr. 2007)104 (4): 982-983).*
Weigert (Invest Ophthalmol Vis Sci (Sep. 2007) 48(9): 4220-4225).*
PCT International Search Report for PCT/EP2010/057493 mailed Oct. 27, 2011.
Klein JA, "Tumescent Technique for Regional Anesthesia Permits Lidocaine Doses of 35 mg/kg for Lipsuction", Journal of Dematologic Surgery and Oncology, Elsevier Science Inc., vol. 16, Mar. 1, 1990 (pp. 248-263).
Naoum C et al. "Dermal Filler Materials and Botulin Toxin", International Journal of Dermatology, Wiley-Blackwell Boublishing Ltd., UK, vol. 40, No. 10, Oct. 1, 2001 (pp. 609-621).

* cited by examiner

*Primary Examiner* — Karlheinz R Skowronek
*Assistant Examiner* — Mindy Newman
(74) *Attorney, Agent, or Firm* — Harris Beach PLLC

(57) ABSTRACT

The present invention concerns an injectable composition comprising a filler or a botulinum toxin and an adrenergic receptor agonist, and its use for diminishing, decreasing or avoiding skin reactions due to injection, specially redness, ecchymosis, bruising, bleeding, erythema, oedema, necrosis, ulceration, swelling and/or inflammation.

33 Claims, 1 Drawing Sheet

INJECTABLE COMBINATION OF ADRENERGIC RECEPTOR AGONISTS WITH FILLERS, FOR DECREASING SKIN REACTIONS DUE TO INJECTION

CROSS-REFERNCE TO RELATED APPLICATIONS

This application is a national stage application under 35 U.S.C. §371 of PCT Application No. PCT/EP2010/057493, filed May 28, 2010, which claims priority to and the benefit of U.S. provisional patent application Ser. No. 61/213,322, filed May 29, 2009, which is incorporated herein by reference in its entirety.

FIELD OF THE INVENTION

The present invention is in the surgical and dermatological domain.

The present invention relates to an injectable composition comprising an adrenergic receptor agonist, preferably brimonidine, and a filler, preferably hyaluronic acid. It concerns its use in preventing and/or treating superficial bruising and bleeding caused by aesthetic procedures.

BACKGROUND OF THE INVENTION

Superficial bruising and, to a lesser extent, bleeding are not uncommon consequences—reported on average about one-third of the time—of many aesthetic procedures, including dermal fillers, botulinum toxins and laser resurfacing.

More significant bruising occurs with surgical procedures such as liposuction, breast augmentations/lifts, face lifts and tummy tucks.

The management of secondary immediate reactions due to subcutaneous or intradermal injection of fillers with vascular damages or vascular breaking wall inducing ecchymosis, bruising, leakage of blood components having immediate action on inflammation setting up, redness and oedema, are of particular interest.

Although redness, erythema, bruising and bleeding are not generally considered as a big problem, most physicians prepare their patients for this possibility by alerting them to it prior to the procedure. Particularly, physicians often caution against using aspirin or other anticoagulant drugs before and after the procedure, extensively use ice packs immediately after the procedure and quite commonly recommend Arnica, an herb used to promote healing. This kind of drawbacks may discourage some patients and particularly towards aesthetic procedures. In particular with regards to the consequences of bruising/bleeding, physicians report that one of the most significant concerns for patients is downtime as when bruising occurs, patients prefer to stay home rather than return to work and social activities Therefore, there is a need for alleviating bruising/bleeding that occur during aesthetic or surgical procedures, especially when fillers are injected.

The present invention is based on the demonstration by the Applicant that the injection of an adrenergic receptor agonist together with the filler reduces the occurrence of skin reactions due to injection.

DESCRIPTION OF THE INVENTION

The present invention provides a combination of quantity of adrenergic receptor agonist, and preferably product known as brimonidine, with fillers or botulinum toxins, and preferably with hyaluronic acid. Said combination is systemically administrated to an individual in need.

The present invention provides the use in an individual in need, of a quantity of adrenergic receptor agonist, and preferably product known as brimonidine, in combination with botulinum toxins or fillers, and preferably with hyaluronic acid.

The present invention provides a method for diminishing or decreasing or avoiding bruising and, to a lesser extent, bleeding and particularly in aesthetic procedures, including dermal fillers and preferably hyaluronic acid, by providing to an individual in need thereof a quantity of adrenergic receptor agonist, and preferably product known as brimonidine.

In a first aspect, the invention concerns a composition comprising:
  a filler or a botulinum toxin;
  an adrenergic receptor agonist.

As it clearly appears from the present description, the present invention concerns the prevention and the treatment of skin defects, especially those due to skin aging (folds, wrinkles, skin depressions, . . . ) or skin damages (scars, . . . ).

Over the last years, the treatment of skin defects has become of great interest. As a result, it has been proposed to intradermally or subcutaneously inject compounds.

As a first possibility, botulinum toxins which are able to provoke muscle paralysis or contraction can be locally injected.

Alternatively and in a preferred embodiment, a filler can be injected. A filler is generally defined as a biomaterial able to fill dermal tissues. The claimed composition to be injected, comprising said filler in an aqueous medium and displaying filling properties, can also be defined as a "dermal filler".

In this context, same compounds like polyacrylamid gels, polymethylmethacrylate (PMMA) particles or silicones can be used.

The most preferred compounds are resorbable molecules such as hyaluronic acid, collagen, alginate, dextran, elastine or polyurethane gels.

Hyaluronic acid or hyaluronate is a non-sulfated glycosaminoglycan widely distributed throughout connective, epithelial, and neural tissues. It is one of the chief components of the extracellular matrix. It contributes significantly to cell proliferation and migration. It plays an important role in skin hydration and skin elasticity. The level of hyaluronic acid decreases with ageing both in quantity and quality, inducing skin drying and wrinkles.

Hyaluronic acid is a naturally occurring biopolymer that forms highly viscous solutions in water. Therefore, it is widely used as a pharmaceutical product. Moreover, this compound is considered to be very safe since no immunogenicity reaction has been observed. So far, few minor adverse events have been noticed.

Therefore and advantageously, the filler is hyaluronic acid or a pharmaceutically acceptable salt or derivative thereof, particularly the sodium or potassium salt. Hyaluronic acid can be used under different forms: salts thereof, derivatives thereof such as esters or amides, in a linear form or cross-linked. In particular, the molecular weight, typically comprised between 500 kDa and 5 000 kDa, and the degree of cross-linking depends on the application, especially on the depth of the wrinkles to be filled.

The second component of the claimed composition is an adrenergic receptor agonist. Adrenergic receptor agonists are known to bind and activate the adrenergic receptors.

As it is well known in the art, adrenergic receptors encompass both $\alpha$ and $\beta$ receptors. Among $\alpha$ adrenoreceptors, $\alpha 1$ and $\alpha 2$ receptors were distinguished in the 1970's. During the same decade, α2 receptors were found to occur on vascular smooth muscles and exhibit mediation of vasoconstrictor response ("Subtypes of functional $α_1$- and $α_2$-adrenoceptors" J R Docherty; European Journal of Pharmacology 361 (1998) 1-15). Thus, molecules exhibiting a adrenergic agonism, advantageously α2 adrenergic agonism, possess peripheral vasoconstrictive activity.

Agonists to be used in the claimed composition can be directed to α and/or β receptors. However, because of their possible side-effects, molecules exhibiting β adrenergic agonism, are advantageously disclaimed. In the rest of the application, a molecule having no affinity for the β adrenergic receptors will be named "an α-adrenergic receptor agonist".

Among the α receptors, the agonist can be an agonist of both α1 and α2 receptors, or can be specific for α1 or α2. Preferably, the chosen molecule displays more affinity for the α2 than for the α1 receptor, and will generally be named, in the rest of the application, "an α2 adrenergic receptor agonist".

In a preferred embodiment, the adrenergic receptor agonist is an adrenergic receptor agonist α2, preferably brimonidine.

Agonists of the α2 adrenoceptors have been used therapeutically for a number of conditions including hypertension, congestive heart failure, angina pectoris, spasticity, glaucoma, diarrhea, and for the suppression of opiate withdrawal symptoms (J. P. Heible and R. R. Ruffolo Therapeutic Applications of Agents Interacting with a-Adrenoceptors, p. 180-206 in Progress in Basic and Clinical Pharmacology Vol. 8, P. Lomax and E. S. Vesell Ed., Karger, 1991).

Adrenoceptor agonists such as clonidine have been primarily used orally, though a patch formulation is known. The α2 agonists are known to mediate vasoconstriction both in the core and periphery of a patient. In particular α2 adrenoceptor agonists are known to cause vasoconstriction of peripheral arterioles, in response to stimulation due to cold or stress.

A number of patents describe the use of brimonidine for treating ophthalmic conditions and eye diseases. In Canadian patent No. CA2326690, there is described the use of topical ophthalmic preparations for use only in the eyes, to treat eye diseases.

As already said above, the most preferred compound in the context of the invention is (5-Bromo-quinoxalin-6-yl)-(4,5-dihydro-1H-imidazol-2-yl)-amine (commonly referred to as brimonidine) and pharmaceutically acceptable salts thereof, particularly the tartrate salt.

Other compounds known to be α2 adrenoceptor agonists and which can be used in the frame of the present invention are: clonidine, apoclonidine.

More generally, other compounds which are a adrenoceptor agonists are: Synephrine, octodrine, vasopressine and analogs, ornipressine, midodrine, phenylephrine, xylometazoline, oxymetazoline, norepinephrine, methoxamine.

Compounds which have also an affinity for the β receptors but which can be used in certain conditions are: epinephrine, ephedrine, etilefrine.

Of course, the pharmaceutically acceptable salts of all these compounds are also encompassed.

According to the instant invention, the term "pharmaceutically acceptable salt (s)", as used herein, means those salts of compounds of the invention that are safe and effective for topical use in mammals and that possess the desired biological activity. Pharmaceutically acceptable salts include salts of acidic or basic groups present in the compounds of the invention.

Pharmaceutically acceptable acid salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Certain compounds of the invention can form pharmaceutically acceptable salts with various amino acids.

Suitable base salts include, but are not limited to, aluminum, calcium, lithium, magnesium, potassium, sodium, zinc, and diethanolamine salts. For a review on pharmaceutically acceptable salts see BERGE ET AL., 66 J. PHARM. Sci. 1-19 (1977).

According to a first embodiment, the claimed composition only contains a filler, or a mixture thereof, and an adrenergic receptor agonist, or a mixture thereof, advantageously hyaluronic acid and brimonidine.

According to an alternative embodiment, the claimed composition also contains one or more additional ingredients.

The one or more other ingredients can be active ingredients, e.g. an anaesthetic. A preferred anaesthetic is lidocaine or a pharmaceutically acceptable salt thereof. Other active ingredients are for example growth factors, peptides, . . .

The claimed composition can also contain other pharmaceutical acceptable ingredients such as carriers, excipients, preservatives, . . .

In one embodiment, the compounds of the invention are administrated to a patient in need thereof by systemic route, preferably by injection. Therefore, in the context of the instant invention the compounds are delivered to the affected area of the skin in a pharmaceutically acceptable carrier. As used herein, a pharmaceutically acceptable carrier is any pharmaceutically acceptable formulation that can be applied to the skin for dermal, intradermal, or transdermal delivery of a pharmaceutical or medicament. The combination of a pharmaceutically acceptable carrier and a compound of the invention is termed an injectable formulation of the invention.

In the frame of the present invention, the composition is a pharmaceutically acceptable injectable formulation. By "pharmaceutically acceptable injectable formulation" it is meant in the context of the invention any formulation which is pharmaceutically acceptable for systemic delivery. Preferably, the composition is administrated in the superficial, middle or deep dermis, by subcutaneous or intradermal route. Typically, the claimed composition consists in a solution or a gel, preferably an aqueous solution or gel.

The claimed composition is composed of or contains therapeutically effective amounts of adrenergic receptor agonists and fillers. As used herein, a "therapeutically effective amount of a compound of the invention" means the minimum amount of the compound that is effective to obtain the desired effect in the context of the invention.

Typically, the claimed composition contains:
a filler, preferably HA, representing 1% to 2.5% by weight of the composition;
an adrenergic receptor agonist, preferably brimonidine, representing 0.0001% to 1% by weight of the composition;
optionally an anaesthetic, representing 0.01% to 3% by weight of the composition As already said, the claimed composition is meant to be administered to a subject or a patient, especially by facial injection (forehead, eyes, nasolabial fold, . . . ). As used herein, the term "subject" or "patient" are used equivalently and means any animal, preferably a mammal, more preferably, a human to whom will be or has been administered compounds or formulations of the invention. The term "mammals" used herein encompasses any mammal.

Therefore, the invention also provides formulations to deliver a systemic dose of the compound to the patient. In practice and for a treatment sequence, the amounts of active compounds are as follows:

for the filler, preferably HA: between 0.05 mg/kg and 2 mg/kg of body weight. It represents from 5 mg to 100 mg.

for the adrenergic receptor agonist, preferably brimonidine: between $5.10^{-3}$ µg and 0.8 mg/kg of body weight. It represents from 0.5 µg to 40 mg.

In a preferred embodiment, the volume of the claimed composition to be injected varies between 0.1 and 10 ml, typically between 0.5 and 4 ml. Preferably, said volume is presented as a single dose syringe. Said injection can be repeated, for example after 4 to 18 months.

Another aspect of the invention is an article of manufacture that comprises a systemic formulation of the invention in a suitable container with labelling and instructions for use. The container is advantageously a single dose syringe.

Preferably, instructions are packaged with the formulations of the invention, for example a pamphlet or package label. The labelling instructions explain how to administer formulations of the invention, in an amount and for a period of time sufficient to treat the patient. Preferably, the label includes the dosage and administration instructions, the formulation's composition, the clinical pharmacology, drug resistance, pharmacokinetics, absorption, bioavailability, and contraindications.

The claimed injectable composition can then be integrated into a kit comprising syringes containing said composition. In said kit, the two active principles, i.e. the filler and the adrenergic receptor agonist, can be presented as a mixture contained in a syringe or can be contained in two separate syringes for extemporaneous mixture.

The claimed composition is advantageously sterilized in conditions suitable for preserving the active principles.

As already said, the claimed composition is dedicated to the prevention and/or treatment of skin defects, especially folds, wrinkles, skin depressions and scars. It concerns a cosmetic or a therapeutic treatment.

According to the invention, it has been shown that the main benefit of the claimed combination is to diminish, decrease or avoid erythema, ecchymosis, bruising or bleeding, especially in connection with the injection of a dermal filler.

Other potential benefits of the claimed composition are as follows:

When the composition further contains an anaesthetic, e.g. lidocaine, the efficiency of said anaesthetic is improved: vasoconstrictive effect provided by the α adrenergic agonist limits anaesthetic diffusion in a large area, thus making anaesthetic efficient in the strict injection site;

By reducing the inflammation, the filler persists longer, possibly due to its slower degradation: the more inflammatory the filler is, the more tissue reaction is severe and higher is the level of inflammatory species, thus degrading faster the filler. Introducing a vasoconstrictive molecule in the filler could limit inflammatory species attraction to the injection site;

A reduction of oedema and swelling is observed: for the same reason as the previous benefit, vasoconstrictive activity of the filler limits liquid flood in reaction to the injection, so hindering liquid concentration nearby the injection site.

More generally, the claimed composition is then intended to diminish, decrease or avoid all the undesirable skin reactions (immediate and/or secondary) due to injection. It indeed includes ecchymosis, bruising or bleeding but also possibly redness, erythema, oedema, necrosis, ulceration, swelling and inflammation.

The claimed composition containing the two active principles can be used simultaneously, separately or sequentially. In other words, the present invention provides a kit of part combining a quantity of adrenergic receptor agonist, and preferably product known as brimonidine, with fillers, and preferably with hyaluronic acid.

In addition to the above, the following examples are provided to illustrate particular embodiments and not to limit the scope of the invention.

EXAMPLES

Legends to Figures

SUMMARY OF THE STUDY

An intracutaneous test of a hyaluronic acid-based dermal filler containing lidocaine and a vasoconstrictor drug (Brimonidine) named RADACT014 was performed in order to evaluate the potential of Brimonidine to reduce the irritation following intradermal injection of filler in the rabbit.

Two adult rabbits received by intracutaneous route 0.2 mL of test product RADACT014 (Test2), NaCl 0.9% (Test5: negative control) and 10LDEEP010 (same hyaluronic acid filler as RADACT014 but with no lidocaine nor Brimonidine; Test1: positive control).

The results obtained with the filler containing Brimonidine (batch RADACT014 (Test2)) are compared with the dermal filler without Brimonidine (positive control: Test 1).

Figure 1:
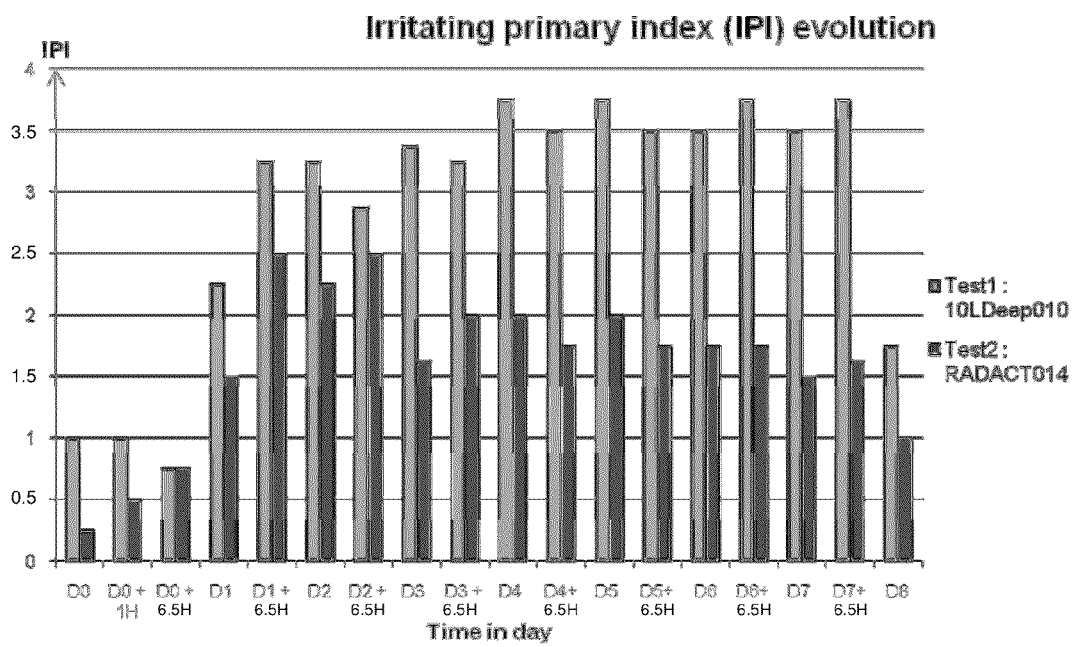
FIG. 1 shows the Irritating Primary Index (IPI) evolution between Day 0 and Day 8 for the claimed composition (Test2) in comparison with a filler alone (Test1).
Figure 2:
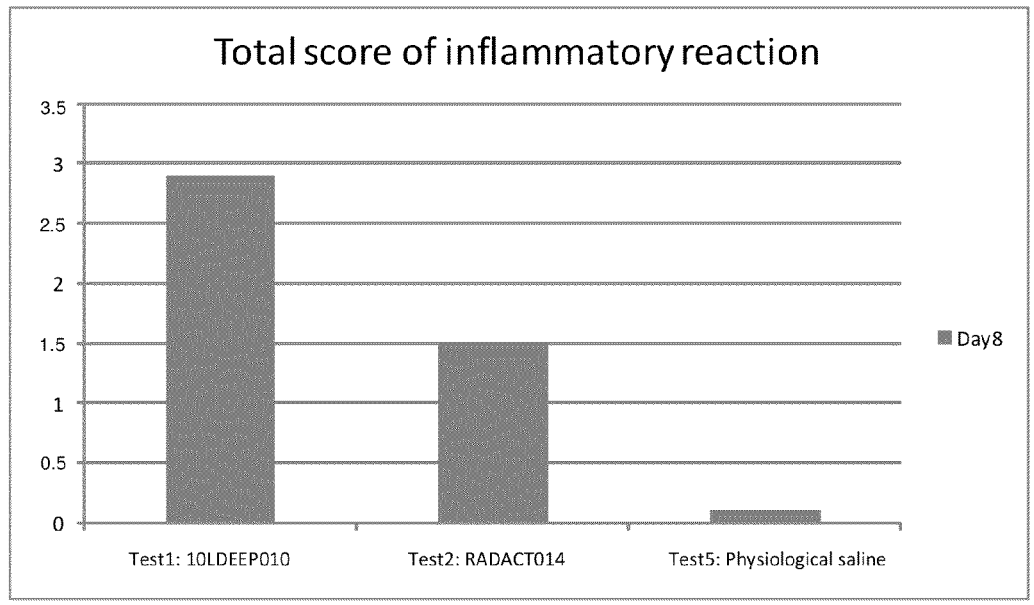
FIG. 2 shows the total score of inflammatory reaction at Day 8 for the claimed composition (Test2) in comparison with a filler alone (Test1).

The sites were examined from Day 0 to Day 8 after injection for gross evidence of tissue reaction, such as erythema, oedema and necrosis (FIG. 1) and the observation of microscopic tissue response done on histological observations after sacrifice at Day 8 (FIG. 2).

The study was conducted according to the requirements of the ISO 10993 standard: Biological Evaluation of medical devices, Part 10: Test for irritation and delayed type hypersensitivity.

Materials and Methods

Preparation of Control Crosslinked Hyaluronic Filler: 10LDEEP010

A crosslinked hyaluronic acid filler 10LDEEP010 (Test1) was obtained by crosslinking with 25% of BDDE a sodium hyaluronate from bacterial origin characterized by a macromolecular weight of around $2\text{-}4\times10^6$ Da. At the end of the crosslinking, a lidocaine hydrochloride was added to the crosslinked hyaluronic acid to reach a concentration of 03%. Homogeneous blend of lidocaine is obtained by extrusion of the mix through mesh. The resulting gel was packed in 1 mL syringes at the concentration of 20 mg/mL and steam sterilized.

Preparation of Crosslinked Hyaluronic Filler Containing Brimonidine: RADACT014

The same crosslinking conditions were applied to the same hyaluronic acid to obtain a filler without lidocaine. In parallel, a 4N sodium hydroxide solution was prepared using 8 g of NaOH and 42 g of purified water. Another solution containing brimonidine and lidocaine was obtained by dissolution of 0.22 g of brimonidine tartrate and 0.33 g of lidocaine hydrochloride in 9.45 mL of phosphate buffer. pH was adjusted to 6 by using the NaOH solution. Then, brimonidine and lidocaine solution was filtered on 0.22 microns.

A filler containing brimonidine and lidocaine, called RADACT014 (Test2), was obtained by gently mixing 5 g of the solution containing the 2 actives and 50 g of the previous crosslinked hyaluronic gel into 3 steps: 5 minutes of mechanical mixing followed by 15 minutes of break and then additional 5 minutes mixing. The resulting gel was packed in 1 mL syringes and steam sterilized. The final concentration of actives was determined after hyaluronidase digestion for brimonidine by HPLC-MS-MS as 0.16% and for lidocaine by HPLC as 0.29%.

Investigation of Immediate Adverse Events Reduction

The potential of irritation reduction by RADACT014 was evaluated in an animal study conducted according to the requirements of the ISO10993-10 requirements: Biological Evaluation of Medical Devices—Test for irritation and delayed type hypersensitivity.

Study Protocol

At Day 0 (D0), two adult rabbits received by intracutaneous route 0.2 mL of test products (Test1: 10LDEEP010 and Test2: RADACT014) and negative control (Test5: physiological saline), injected using a 27G needle. In these conditions, 4 sites were injected for each product.

Then, the injected sites were examined twice a day from Day 0 to Day 8 for gross evidence of tissue reaction such as erythema, oedema, ulceration and necrosis, attributing a score with the following criterions:

| Criterion | Control method | Scale |
|---|---|---|
| Formation of oedema | Visual assessment | (0) none |
| | | (1) slight |
| | | (2) moderate |
| | | (3) marked |
| | | (4) severe |
| Formation of erythema, ulceration and necrosis | Visual assessment | (0) none |
| | | (1) slight |
| | | (2) moderate |
| | | (3) marked |
| | | (4) severe |

At Day 8, the animals were euthanized and injection sites were collected and fixed for histological analysis. Microscopic analyses were performed to assess the following criterions:

| Criterion | Control method | Scale |
|---|---|---|
| Type of cell/implant reaction, local tolerance: | Histological analysis | Score from 0 to 4 for each criterion |
| ✓Fibrin | | (0) None |
| ✓Necrosis | | (1) slight |
| ✓Tissue degeneration | | (2) moderate |
| ✓Granulocyte | | (3) marked |
| ✓PMN eosinophils | | (4) severe |
| ✓Lymphocytes | | |
| ✓Plasmocytes | | |
| ✓Macrophages | | |
| ✓Giant cells | | |
| ✓Fibrocytes | | |
| ✓Neovessels | | |
| ✓Peri and intra-implant tissue | | |
| ✓reconstruction | | |
| ✓Degradation of the material | | |

Results Exploitation

No oedema, nor necrosis occurred in this study. Moreover, only 10LDEEP010 showed a slight and persistent ulceration from day 2 to day 8.

1. Irritation Primary Index (IPI)

IPI of test product is determined for each observation time in the following way:

$$IPI_{Test} = \frac{\sum (\text{oedema score} + \text{erythema score})}{\text{Observations number}} - IPI_{negative\ control}$$

Negative control being test5: physiological saline
$IPI_{negative\ control}$ quotes 0 for each observation time.
The results obtained are shown in FIG. 1.

10LDEEP010 (Test1) showed the highest value of irritation index during the experiment: the index increases between Day 0 and Day 1 and then remains stable. This product is very irritant.

Test2 Product, called RADACT014 and containing Brimonidine, showed the lowest value of IPI: it increases between Day 0 and Day 2 and then stabilizes to Day 7 and finally decreases at Day 8.

RADACT014 showed a reduction of inflammatory effect of the dermal filler from Day 3 in a pronounced and persistent way, thus demonstrating the positive effect of Brimonidine regarding irritation.

2. Histological Analysis

Total scores of inflammation were determined from histological observations according to local tolerance-representative cells type and quantities.

FIG. 2 represents total score of inflammation of each product.

At Day 8, moderate (10LDEEP010) to limited (RADACT014) inflammatory infiltrates were noted, the main cell population being macrophages with a few eosinophils. No specific reaction was observed for the negative control (physiological saline, Test5).

3. Conclusion

This study has shown that the dermal filler (Test1: 10LDeep010) injected in the dermal compartment provokes some inflammatory response with slight ulceration. By incorporating an active molecule (Brimonidine) in this kind of dermal filler (RADACT014), it is possible to reduce the inflammatory response. The gross evidence (erythema, oedema, ulceration and necrosis) and the histological analyses demonstrate both the benefit provided by using the Brimonidine molecule in combination with the filler.

The invention claimed is:

1. An injectable composition for treating a skin defect comprising:
   i. hyaluronic acid (HA);
   ii. an α-adrenergic receptor agonist; and
   iii. an anaesthetic, wherein the anaesthetic is lidocaine or a pharmaceutically acceptable salt thereof.

2. The composition of claim 1, wherein the α-adrenergic receptor agonist is an α2-adrenergic receptor agonist.

3. The composition of claim 1, wherein the composition comprises HA, wherein the HA represents 1% to 2.5% by weight of the composition.

4. A kit comprising one or more syringes and the composition of claim 1.

5. A method for treating a skin defect comprising the step of injecting simultaneously an individual in need thereof with:
   i. hyaluronic acid (HA);
   ii. an α-adrenergic receptor agonist; and iii. an anaesthetic, wherein the anaesthetic is lidocaine or a pharmaceutically acceptable salt thereof.

6. A method for diminishing, decreasing or avoiding a skin reaction in an individual due to injection of a dermal filler, comprising the step of injecting simultaneously:
   i. hyaluronic acid (HA);
   ii. an α-adrenergic receptor agonist; and
   iii an anaesthetic, wherein the anaesthetic is lidocaine or a pharmaceutically acceptable salt thereof.

7. The composition of claim 2, wherein the α2-adrenergic receptor agonist is brimonidine.

8. The composition of claim 1 wherein the lidocaine or the pharmaceutically acceptable salt thereof represents 0.01% to 3% by weight of the composition.

9. The composition of claim 1, wherein the α-adrenergic receptor agonist is brimonidine, xylometazoline, or oxymetazoline.

10. The method of claim 5 wherein the skin defect is a fold, wrinkle, skin depression or scar.

11. The method of claim 6 wherein the skin reaction due to injection is redness, ecchymosis, bruising, bleeding, erythema, oedema, necrosis, ulceration, swelling and/or inflammation.

12. The method of claim 5, wherein the α-adrenergic receptor agonist is an α2-adrenergic receptor agonist.

13. The method of claim 12, wherein the α2-adrenergic receptor agonist is brimonidine.

14. The method of claim 5, wherein the α-adrenergic receptor agonist is brimonidine, xylometazoline, or oxymetazoline.

15. The method of claim 6, wherein the α-adrenergic receptor agonist is an α2-adrenergic receptor agonist.

16. The method of claim 15, wherein the α2-adrenergic receptor agonist is brimonidine.

17. The method of claim 6, wherein the α-adrenergic receptor agonist is brimonidine, xylometazoline, or oxymetazoline.

18. An injectable composition for treating a skin defect comprising:
   i. a botulinum toxin;
   ii. an α-adrenergic receptor agonist; and
   iii an anaesthetic, wherein the anaesthetic is lidocaine or a pharmaceutically acceptable salt thereof.

19. The composition of claim 18, wherein the a-adrenergic receptor agonist is an α2-adrenergic receptor agonist.

20. A kit comprising one or more syringes and the composition of claim 18.

21. A method for treating a skin defect comprising the step of injecting simultaneously an individual in need thereof with:
   i. a botulinum toxin;
   ii. an α-adrenergic receptor agonist; and
   iii an anaesthetic, wherein the anaesthetic is lidocaine or a pharmaceutically acceptable salt thereof.

22. A method for diminishing, decreasing or avoiding a skin reaction in an individual due to injection of a dermal filler, comprising the step of injecting simultaneously:
   i. a botulinum toxin;
   ii. an α-adrenergic receptor agonist; and
   iii an anaesthetic, wherein the anaesthetic is lidocaine or a pharmaceutically acceptable salt thereof.

23. The composition of claim 19, wherein the α2-adrenergic receptor agonist is brimonidine.

24. The composition of claim 18 wherein the lidocaine or the pharmaceutically acceptable salt thereof represents 0.01% to 3% by weight of the composition.

25. The composition of claim 18, wherein the a-adrenergic receptor agonist is brimonidine, xylometazoline, or oxymetazoline.

26. The method of claim 21 wherein the skin defect is a fold, wrinkle, skin depression or scar.

27. The method of claim 22 wherein the skin reaction due to injection is redness, ecchymosis, bruising, bleeding, erythema, oedema, necrosis, ulceration, swelling and/or inflammation.

28. The method of claim 21, wherein the α-adrenergic receptor agonist is an α2-adrenergic receptor agonist.

29. The method of claim 28, wherein the α2-adrenergic receptor agonist is brimonidine.

30. The method of claim 21, wherein the α-adrenergic receptor agonist is brimonidine, xylometazoline, or oxymetazoline.

31. The method of claim 22, wherein the α-adrenergic receptor agonist is an α2-adrenergic receptor agonist.

32. The method of claim 31, wherein the α2-adrenergic receptor agonist is brimonidine.

33. The method of claim 22, wherein the α-adrenergic receptor agonist is brimonidine, xylometazoline, or oxymetazoline.

* * * * *